(12) United States Patent
Aronsson et al.

(10) Patent No.: US 6,575,012 B1
(45) Date of Patent: Jun. 10, 2003

(54) METHOD AND APPARATUS FOR MEASURING A GASEOUS COMPONENT EMANATING FROM A VEHICLE

(75) Inventors: Anders Aronsson, Torslanda (SE); Gregory Scott Horne, Brownstown Township, MI (US); Philip J Johnson, Ann Arbor, MI (US); Thomas Joseph Luley, Grosse Ile, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 09/682,962

(22) Filed: Nov. 2, 2001

(51) Int. Cl.$^7$ ................................................ G01N 7/00
(52) U.S. Cl. ...................................................... 73/23.31
(58) Field of Search ............................... 73/118.1, 49.7, 73/117.1, 23.2, 23.31, 195, 865.6, 116; 340/438, 439; 123/518

(56) References Cited

U.S. PATENT DOCUMENTS

| | | | | |
|---|---|---|---|---|
| 5,167,146 A | * | 12/1992 | Hostetter | 73/117.1 |
| 5,369,976 A | * | 12/1994 | Ratton | 73/116 |
| 5,388,453 A | * | 2/1995 | Ratton et al. | 73/117.1 |
| 5,592,372 A | * | 1/1997 | Artail et al. | 700/73 |
| 6,085,582 A | * | 7/2000 | Tripathi et al. | 73/116 |
| 6,148,656 A | * | 11/2000 | Breton | 73/118.1 |
| 6,435,019 B1 | * | 8/2002 | Vojtisek-Lom | 73/118.1 |
| 6,439,040 B1 | * | 8/2002 | Garms et al. | 73/118.1 |
| 6,446,615 B2 | * | 9/2002 | Stegmann et al. | 123/198 D |

* cited by examiner

Primary Examiner—Hezron Williams
Assistant Examiner—Corey D. Mack
(74) Attorney, Agent, or Firm—Diana D. Brehob

(57) ABSTRACT

A system and method is disclosed for measuring mass of hydrocarbons from point source contributions to overall hydrocarbon emissions from an automotive vehicle at rest.

26 Claims, 2 Drawing Sheets

METHOD AND APPARATUS FOR MEASURING A GASEOUS COMPONENT EMANATING FROM A VEHICLE

BACKGROUND OF INVENTION

The present invention relates generally to a system and method for determining the hydrocarbon emission from point sources located within an automotive vehicle.

It is known to those skilled in the art that an automotive vehicle at rest releases hydrocarbons to the atmosphere which may be fuel, lubricant, or polymer based, the latter emanating from plastic components. The mass of hydrocarbons emanating from a vehicle at rest is typically determined by placing the vehicle in a test facility and performing a Sealed Housing for Evaporative Determination (SHED) test procedure, in which gases within the test facility are drawn into a flame ionization detector (FID) periodically over a 72-hour test period. Based on the concentration of hydrocarbons detected by the FID and the SHED volume, the mass of hydrocarbons emitted by the vehicle can be determined.

The inventors of the present invention have recognized a need to measure the mass of hydrocarbons emanating from discrete portions of a vehicle. Stringent emission regulations, which limit hydrocarbon emission, necessitate the capability to precisely measure all hydrocarbon sources. For example, hydrocarbons may be emitted from the vehicle through the vehicle's air induction system (AIS). Hence, it is desirable to measure the mass of hydrocarbon material emanating from the AIS to substantially ensure that the vehicle is in compliance with these emission regulations, to allow diagnostic tests to be conducted, and to allow various designs to be evaluated.

It has previously been attempted to measure point source or subassembly emissions by forcibly drawing out hydrocarbon material from the subassembly. These have been found to provide a false indication of the amount of hydrocarbons. Furthermore, these prior methods to measure subassembly emission of hydrocarbons: are complex, are costly, and require a relatively extensive amount of modification to the vehicle. Such methods may also interfere with the normal operation of the vehicle, eg., testing other than SHED testing.

The inventors of the present invention have determined a method and apparatus for determining point source hydrocarbon emissions without intrusion upon the normal operation of the vehicle or the results of the SHED test.

SUMMARY OF INVENTION

Disadvantages of prior art systems are overcome by a system for measuring an amount of material emitted from a portion of a vehicle, which includes: a collection fixture coupled to the portion of the vehicle, a sampling tube fitted to the collection fixture; a pump coupled to the sampling tube for drawing gases near the portion of the vehicle to which the collection fixture is coupled and an analyzer for receiving the gases and for producing a concentration signal proportional to the concentration of the material pumped through the analyzer.

The present invention further provides a method for measuring a flow rate of hydrocarbons emitted from a portion of a vehicle wherein a pump draws gases from the portion of the vehicle. In the method an indication of a flow rate of the gases and an indication of hydrocarbon concentration of the gases are provided. Based on the flow rate and concentration, a flow rate of hydrocarbons emitted from the portion of the vehicle can be determined.

A primary advantage of the present invention is that this method and apparatus permits an accurate determination of the role of a vehicle subassembly or point source in contributing to the overall vehicle hydrocarbon emissions.

A further advantage is that the present invention does not impair the measurement accuracy of the vehicle's total hydrocarbon emission in the SHED test.

Yet another advantage is that the intrusion upon the vehicle and the modifications required are minimal. For example, to make such a measurement on the AIS, a tube is inserted into an air intake conduit. The tube may be left in place and still allow the vehicle to be normally operated or tested for other purposes.

Another advantage of the present invention is that the point source or subassembly of the vehicle that is being tested need not be removed from the vehicle to determine the hydrocarbon emission from the point source during the SHED test. Furthermore, a special test facility is not required to perform point source or subassembly measurements as the SHED test facility may be used for this purpose. Additionally, the point source hydrocarbons may be measured concurrently with the total vehicle hydrocarbon measurements; thus, efficiently employing a SHED test facility.

A further advantage is that the measuring apparatus is not complicated or expensive.

The above advantages and other advantages, objects, and features of the present invention will be readily apparent from the following detailed description of the preferred embodiments when taken in connection with the accompanying drawings.

BRIEF DESCRIPTION OF DRAWINGS

The advantages described herein will be more fully understood by reading an example of an embodiment in which the invention is used to advantage, referred to herein as the Detailed Description, with reference to the drawings wherein.

DETAILED DESCRIPTION

Figure 1:
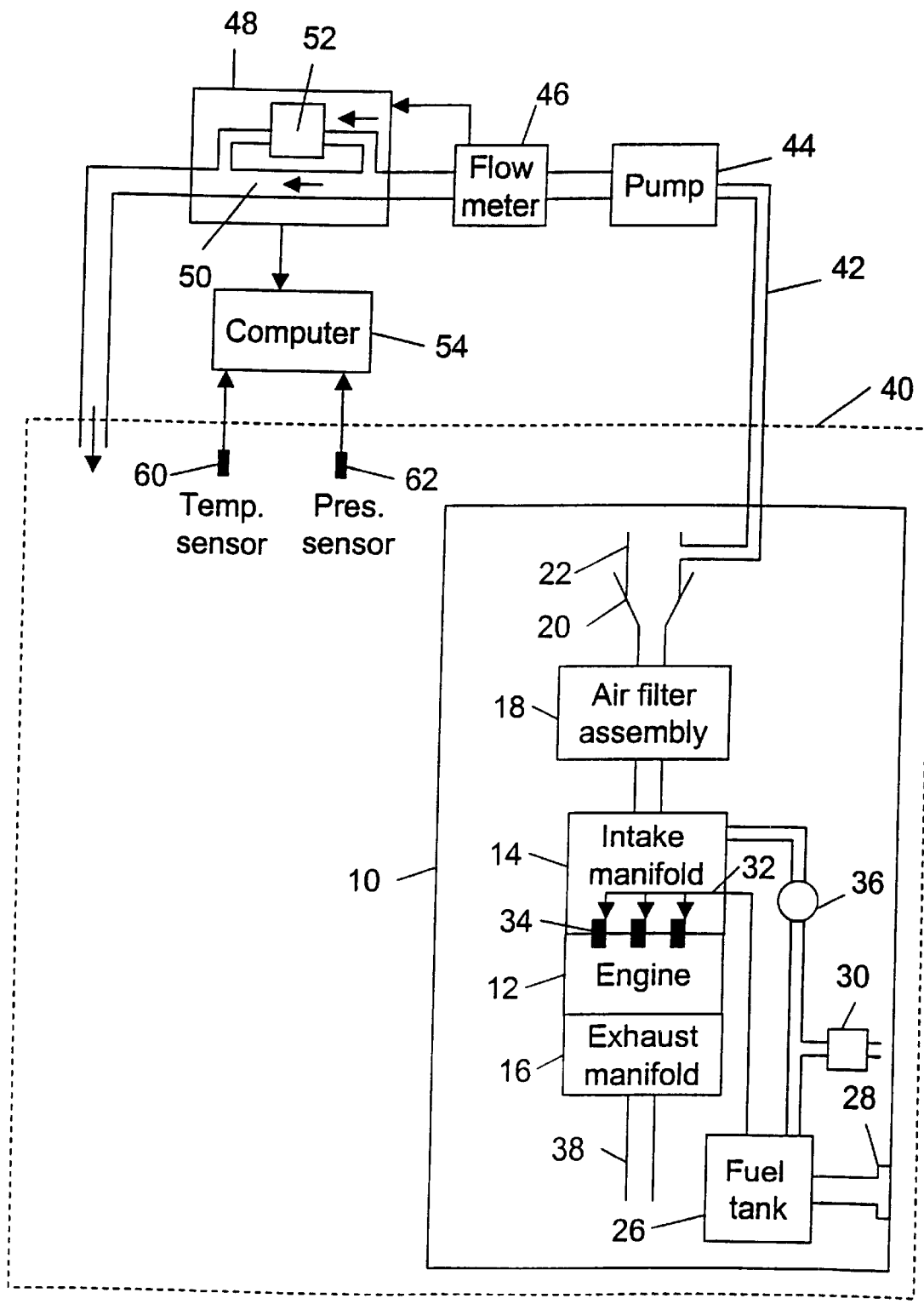
FIG. 1 is a schematic of the SHED test facility in which the vehicle is contained and the associated hardware to ascertain hydrocarbon emissions from one of the vehicle's subassemblies, according to an aspect of the present invention.

Referring to FIG. 1, the SHED test facility 40 contains vehicle 10. Vehicle 10 is equipped with engine 12, an inline 3-cylinder in the present example. During the SHED test, the engine is not operating. However, to understand the relationship of vehicle 10 hardware, the components will be discussed in relation to an operating vehicle. Engine 12 inducts air from the atmosphere through bell mouth 20 into air filter assembly 18 and into intake manifold 14. Engine 12 exhausts combusted gases through exhaust manifold 16 and discharges the gases to the atmosphere through exhaust pipe 38. Engine 12 receives fuel from fuel tank 26 through fuel lines, fuel rail 32, and injectors 34. FIG. 1 indicates injectors 34 supplying fuel to engine 12 directly, i.e., a direct injection engine. The present invention applies as well to port injection configurations in which injectors 34 supply fuel into intake manifold 14.

Vehicle 10 is fueled through filler cap 28 and fuel flows into fuel tank 26. Fuel tank 26 is coupled to a carbon canister 30 which receives vapors emanating from fuel tank 26. Fuel tank 26 emits vapors, typically, during fuel filling when vaporized fuel above the liquid fuel is displaced and also due to temperature changes affecting the vapor pressure in fuel tank 26. These hydrocarbon vapors exiting fuel tank 26 are conducted into carbon canister 30. Typically carbon canister 30 stores hydrocarbon vapors for a period and is subsequently purged of hydrocarbon vapors. During the purge portion of the cycle, valve 36 is opened. A depressed pressure in intake manifold 14 causes fresh air to be drawn through carbon canister 30, so as to strip off stored hydrocarbon vapors. This gaseous mixture is inducted into intake manifold 14 and combusted in engine 12.

The method and system of the present invention may be used to measure various point sources. By way of example, the configuration shown in FIG. 1 may be used to isolate hydrocarbons from the air induction system (AIS). The AIS includes elements 14, 18, and 20 of FIG. 1.

In FIG. 1, tube 22 is inserted into bell mouth 20. The interface between tube 22 and bell mouth 20 is well sealed so that the gases collected are from the AIS. Tube 22 provides a location proximate to the AIS for tube 42 to be coupled. Sampled gases are pulled into pump 44 via tube 42. The volume of extracted gases is measured in flow meter 46, and the gases are then directed into flame ionization detector (FID) 48. Within FID 48, a fraction of the flow passes through chamber 52 which contains a hydrogen-air flame. The hydrocarbons in the extracted gases are combusted and become ionized. By measuring ionization level, FID 48 provides a measure of the amount of hydrocarbons fed to it. Within FID 48, the majority of the extracted gases, however, bypass chamber 52 and are exhausted from FID 48 unreacted. The gases exhausted from FID 48 are discharged back into SHED test facility 40 so that the hydrocarbons, less the fraction consumed in chamber 52, extracted by pump 44 are returned to SHED test facility 40 to ensure the integrity of the test.

A second measurement system (not shown), which includes elements analogous to 42, 44, 46, 48, 50, 52, and 54, is used to measure the concentration of the hydrocarbon material within SHED test facility 40, i.e., the background or total vehicle concentration. In this way, the hydrocarbons emanating solely from the AIS can be accurately determined. The second measurement system need only be operated periodically to determine the background hydrocarbon concentration.

The mass emission rate of hydrocarbons from the AIS is computed by computer 54 of FIG. 1 as:

$$m=(C_{ps}-C_{bkg})*Q*P*MW/(R*T)$$

where m is the mass emission flow rate of hydrocarbons, C is the concentration (unitless, eg., ppm), Q is the volumetric flow rate, P is the pressure in the SHED test facility 40, MW is the molecular weight, R is the universal gas constant, and T is the temperature in the SHED test facility 40. MW refers to the molecular weight of hydrocarbons; however, since the hydrocarbons are a mixture of species, it is difficult to find a number to characterize the mixture. It is common practice to characterize the hydrocarbons in terms of a single hydrocarbon species. As an example, the calibration gas used in FID 48 may be propane, $C_3H_8$, in which case, MW is 44. The subscripts, ps and bkg, in the above equation, refer respectively to the point source concentration measured via the test configuration shown in FIG. 1 and to the background reading which is measured by an alternate set of measuring hardware as discussed above. In the embodiment shown in FIG. 1, FID 48 receives a signal of flow rate from flow meter 46. FID 48 transmits both flow rate and concentration signals to computer 54. Alternatively, the flow rate signal from flow meter 46 could be transmitted to computer 54 directly. Pressure and temperature are determined via temperature sensor 60 and pressure sensor 62 within SHED test facility 40.

The total mass of hydrocarbons emitted from the point source may be determined by calculating the mass flow rate of hydrocarbons, using the equation above, over a short time period, for example 10 seconds and then multiplying the flow rate by the sample period.

The result is the mass of hydrocarbons emitted during that time period. The total mass of hydrocarbons can be determined by summing the mass results from all of the individual time periods for the duration of the SHED test.

Those skilled in the art will recognize that FID 48 is one type of analyzer that could be used to determine HC concentration. Other analyzers, such as thermal conductivity sensors, non-dispersive infrared detectors, or others could be used in place of FID 48 To maintain the integrity of the SHED test, the present invention should not substantially affect the SHED procedure. As mentioned above, the gases that are extracted from SHED test facility 40 into chamber 52 of FID 48 are returned to SHED test facility 40 without the fraction of hydrocarbons going through the burner or chamber 52. The fraction of hydrocarbons consumed in chamber 52 can be computed as:

$$f=b*Q*d*t/V$$

where f is the fraction of total SHED hydrocarbons consumed, b is the fraction of the gases fed to FID 48 which enter chamber 52, Q is pump 44 flow rate, d is the duty cycle of pump 44 (eg., d=1.0 if pump 44 is employed continuously), t is the time since the initiation of the test, and V is the volume of SHED test facility 40. The value of f should be maintained less than about 0.01 (or 1%) to ensure SHED test integrity. An example of typical numbers: FID draws 5% of the flow into chamber 52 (b=0.05); the flowrate is 6.4 ft³/hr; the duty cycle is 100% (d=1.0); the time of the test is 72 hours; and the volume of SHED test facility is 2500 ft³. The resulting f=0.009 is within the required value for f.

Figure 2:
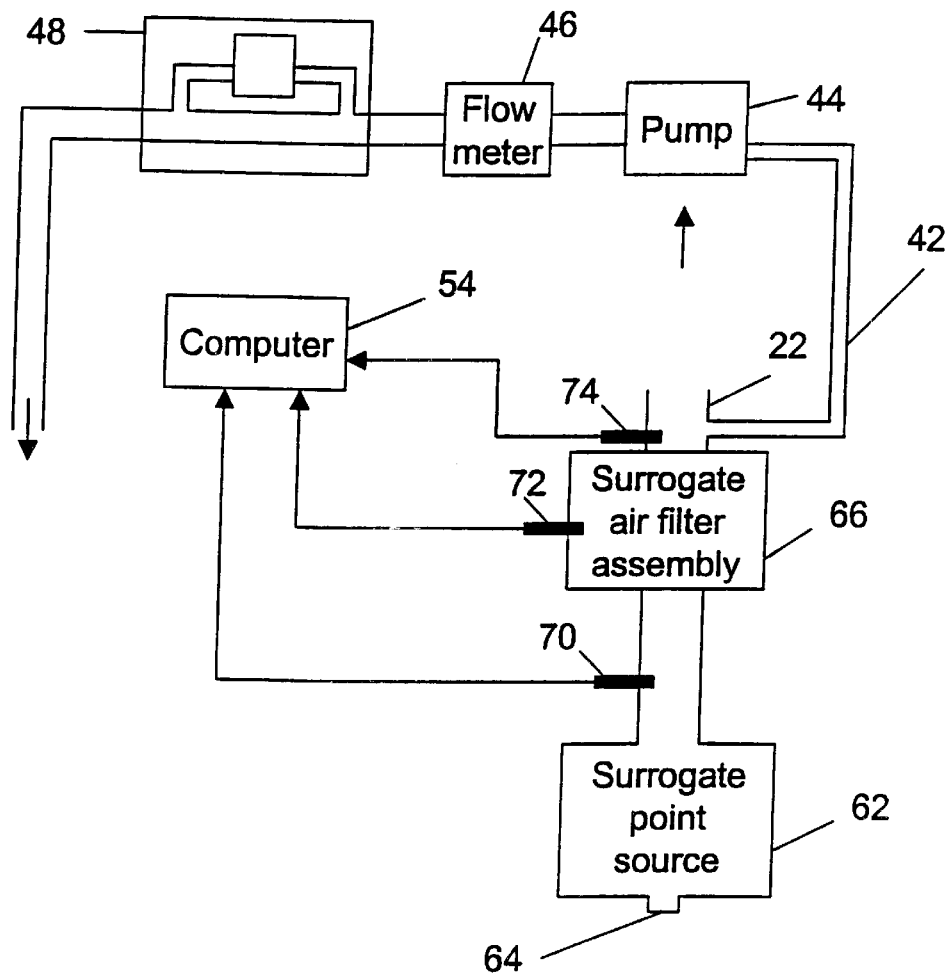
FIG. 2 is a schematic of the test setup employed to verify the method described herein.

To determine whether the point source test procedure, disclosed herein, interferes with the natural vaporization processes, a test assembly was constructed and is shown in FIG. 2.

Figure 3:
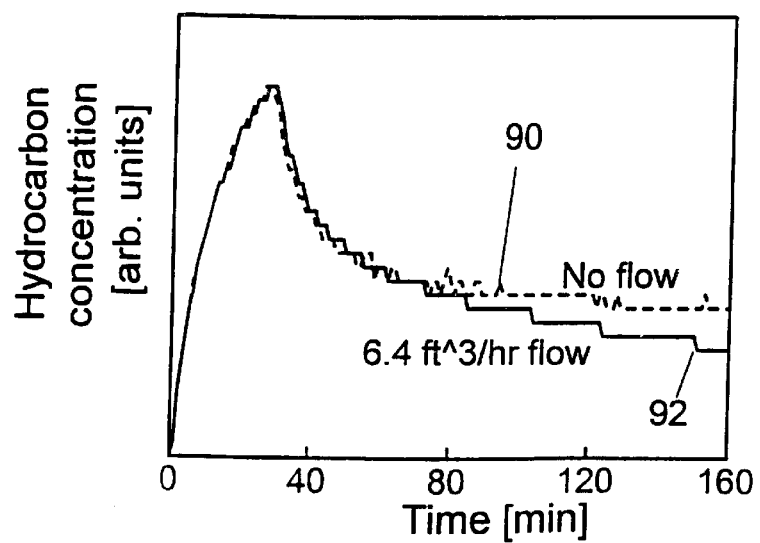
FIG. 3 is a graph of pentane concentration detected over time at a particular location in the test setup.

Vessel 62 is a surrogate point source, i.e., it may simulate intake manifold 14 or other point sources. At the bottom of vessel 62 is a small cup 64 into which a few milliliters of a hydrocarbon may be placed. Surrogate point source 62 is connected to a surrogate air filter assembly 66. These are connected to the test apparatus that were previously shown and discussed in regards to FIG. 1: pump 44, flow meter 46, and FID 48. Hydrocarbon sensors 70, 72, and 74 are installed near the surrogate point source 62, the surrogate air filter assembly 66, and bell mouth 22, respectively. Hydrocarbon sensors 70, 72, and 74 may be thermal conductivity type sensors. The tests were conducted by placing several milliliters of pentane into cup 64 within vessel 62. Pentane was chosen because it is a very volatile hydrocarbon. The test was conducted twice, once with pump 44 drawing gases through tube 42 and once without pump 44 operating, using an identical volume of pentane for both runs. Referring to FIG. 3, hydrocarbon sensor 74 gave similar results regardless of whether pump 44 was operating or not. That means that operation of the sampling apparatus (elements 44, 46, and 48) has neglible impact on the amount of hydrocarbons at location 74. Although not shown herein, hydrocarbon sensors 70 and 72 also were found to detect substantially identical hydrocarbon levels over the duration of the test with pump 44 operating or not.

The present invention has been described in regards to measuring a particular point source, namely, the AIS. However, other point sources may also be measured by the invention described herein. For example, shrouds or other collection fixtures could be constructed to measure other point sources, including but not limited to: fuel rail 32 and fuel injectors 34, fuel filler cap 28, and carbon canister 14.

While several modes for carrying out the invention have been described in detail, those familiar with the art to which this invention relates will recognize alternative designs and embodiments for practicing the invention. The above-described embodiments are intended to be illustrative of the invention, which may be modified within the scope of the following claims.

What is claimed is:

1. A system for measuring an amount of material emitted from a selected portion of a vehicle comprising:
   a collection fixture coupled to the selected portion of the vehicle;
   a sampling tube fitted to said collection fixture;
   a pump coupled to said sampling tube for drawing gases proximate to the selected portion of the vehicle to which the collection fixture is coupled with the vehicle in a substantially sealed test facility; and
   an analyzer coupled to an outlet of said pump for receiving said gases and for producing a concentration signal proportional to the concentration of the material pumped through the analyzer with the vehicle and said collection fixture enclosed in said sealed test facility.

2. The system of claim 1 further comprising:
   a flow meter which provides a flow rate signal proportional to a flow rate through said pump; and
   an electronic computer, operably connected to said flow meter and said analyzer, which computes said amount of material based on said concentration signal and said flow rate signal.

3. The system of claim 2 wherein said electronic computer is operably connected to a temperature sensor and a pressure sensor and said computation of said amount of material is based on an output of said temperature sensor and an output of said pressure sensor.

4. The system of claim 1 wherein said material is a hydrocarbon.

5. The system of claim 1 wherein said amount is a mass flow rate.

6. The system of claim 1 wherein the selected portion of the vehicle is an air intake system and said collection fixture is a collection tube coupled to said air intake system.

7. The system of claim 6 wherein a diameter of said collection tube is substantially similar to a diameter of an inlet of said air intake system and a length of said collection tube is greater than 3 centimeters and less than 15 centimeters in length so that said collection tube does not substantially interfere with a mass of hydrocarbon emitted from the selected portion of the vehicle.

8. The system of claim 1 wherein the selected portion of the vehicle is a fuel filler apparatus.

9. The system of claim 1 wherein the selected portion of the vehicle is a fuel rail and fuel injectors coupled to said fuel rail.

10. The system of claim 1 wherein said analyzer and pump are located outside said sealed test facility and said sampling tube passes through said sealed test facility.

11. The system of claim 1 wherein the vehicle has an engine and said engine is not operating.

12. A method for measuring a flow rate of hydrocarbons emitted from a selected portion of a vehicle, wherein a pump draws gases from the selected portion of the vehicle, comprising the steps of:
   providing an indication of a pump flow rate of the gases with the vehicle in a substantially sealed test facility;
   providing an indication of a concentration of hydrocarbons in the gases; and
   determining the flow rate of hydrocarbons emitted from the selected portion of the vehicle based on said pump flow rate and said concentration of hydrocarbons, with the vehicle enclosed in said sealed test facility.

13. The method of claim 12 wherein said indication of said concentration of hydrocarbons is provided by a flame ionization detector.

14. The method of claim 13 wherein said sealed test facility is of a predetermined volume.

15. The method of claim 14 further comprising the steps of:
   providing an indication of temperature within said sealed test facility;
   providing an indication of pressure within said sealed test facility; and
   computing the flow rate of hydrocarbons emitted from the selected portion of the vehicle based on said pump flow rate, said concentration of hydrocarbons, said temperature, and said pressure.

16. The method of claim 14 wherein said gases are removed from said sealed test facility and introduced into a flame ionization detector, with an effluent stream from said flame ionization detector being conducted into said sealed test facility.

17. The method of claim 16 wherein a fraction of said gases introduced into said flame ionization detector passes through a flame section of said flame ionization detector.

18. The method of claim 15 wherein a flow rate of said fraction of said gases is less than a predetermined flow rate.

19. The method of claim 18 wherein said predetermined flow rate is 1% of said predetermined volume of said sealed test facility divided by a test duration.

20. The method of claim 10 wherein a mass of hydrocarbons emitted from the selected portion of the vehicle is computed based on a time history of said flow rate of hydrocarbons.

21. The method of claim 10 wherein the selected portion is a carbon canister coupled to a vehicle fuel tank disposed in the vehicle and said collection fixture is coupled to said carbon canister.

22. A system for measuring an amount of gases emitted from a selected one of a plurality of regions of a vehicle which emit gases, comprising:
   a collection fixture coupled to a selected one of the regions of the vehicle;
   a sampling tube fitted to said collection fixture;
   a pump coupled to said sampling tube for drawing gases proximate to the selected one of the regions to which the collection fixture is coupled, with the vehicle in a non-operating condition; and an analyzer coupled to an outlet of said pump for receiving said gases and for producing a concentration signal proportional to the concentration of the material pumped through the analyzer.

23. The system of claim 22 wherein said vehicle has an engine and said non-operating condition occurs when said engine is not rotating.

24. The system of claim 22 wherein said gases are hydrocarbons.

25. A method for measuring a flow rate of hydrocarbons emitted from a selected one of a plurality of regions of a vehicle, wherein a pump draws gases from the selected one of regions of the vehicle, comprising the steps of:

providing an indication of a pump flow rate of the gases emitted from the selected one of the regions with the vehicle in a non-operating condition; and providing an indication of a concentration of hydrocarbons in the gases; and determining the flow rate of hydrocarbons emitted from the portion of the vehicle based on said pump flow rate and said concentration of hydrocarbons.

26. The system of claim 25 wherein said vehicle has an engine and said non-operating condition occurs when said engine is not rotating.

* * * * *